United States Patent [19]

Porges

[11] Patent Number: 4,510,944

[45] Date of Patent: Apr. 16, 1985

[54] METHOD AND APPARATUS FOR EVALUATING RHYTHMIC OSCILLATIONS IN APERIODIC PHYSIOLOGICAL RESPONSE SYSTEMS

[76] Inventor: Stephen W. Porges, 1407 Grandview, Champaign, Ill. 61820

[21] Appl. No.: 454,536

[22] Filed: Dec. 30, 1982

[51] Int. Cl.³ .............................................. A61B 5/02
[52] U.S. Cl. .................................... 128/687; 128/671
[58] Field of Search ............................... 128/702–703, 128/705–706, 708, 687, 695–696, 698, 670–671

[56] References Cited

U.S. PATENT DOCUMENTS

| | | | |
|---|---|---|---|
| 3,599,628 | 8/1971 | Abbenante | 128/698 |
| 3,633,569 | 1/1972 | Brayshaw | 128/702 |
| 3,779,237 | 12/1973 | Goeltz et al. | 128/702 |
| 3,811,428 | 5/1974 | Van Horn et al. | 128/698 |
| 3,824,990 | 7/1974 | Baule | 128/702 |
| 3,881,467 | 5/1975 | Stanly et al. | 128/702 |
| 4,231,374 | 11/1980 | Hudek et al. | 128/702 |
| 4,261,370 | 4/1981 | Von Nettelhorst | 128/702 |
| 4,336,810 | 6/1982 | Anderson et al. | 128/702 |

OTHER PUBLICATIONS

"The Influence of Methylphenidate on Spontaneous Autonomic Activity and Behavior in Children Diagnosed as Hyperactive", Porges et al., *Psychophysiology*, vol. 18, No. 1, 1981.

"Heart Period Variability During Estrogen Exposure and Withdrawal in Female Rats", McCabe et al., *Physiology & Behavior*, vol. 26, pp. 535–538, 1981.

"The Effects of Pharmacological Manipulations that Influence Vagal Control of the Heart on Heart Period, Heart–Period Variability and Respiration in Rats", Yongue et al., *Psychophysiology*, vol. 19, No. 4, 1982.

"Respiratory–Heart Rate Interactions: Psycholophysiological Implications for Pathophysiology and Behavior", Porges et al., in J. Cacioppo & R. Petty (Eds.), *Perspectives in Cardiovascular Psychophysiology*, New York: Guilford Press, May 1982.

"The Application of Time–Series Statistics to Psychological Research: An Introduction", Bohrer et al., In G. Keren (Eds.), *Statistical and Methodological Issues in Psychology and Social Science Research*, Hillsdale, NJ, Lawrence Erlbaum & Assoc., Apr. 1982.

"Time–Series", M. G. Kendall, Charles Griffin & Company, Ltd., London, 1973.

"The Ontogeny of Heart Period Patterning in the Rat", Larson et al., *Developmental Psychobiology*, Nov. 1982.

Kitney et al., "Heart Rate Variability in the Assessment of Autonomic Diabetic Neuropathy"; *Automedica*, vol. 4, 1982, pp. 155–167.

Sayers; "Analysis of Heart Rate Variability"; *Ergonomics*, vol. 16, No. 1, 1973, pp. 17–32.

*Primary Examiner*—Lee S. Cohen
*Assistant Examiner*—Angela D. Sykes
*Attorney, Agent, or Firm*—Oblon, Fisher, Spivak, McClelland & Maier

[57] ABSTRACT

A method and apparatus is disclosed for detecting amplitude variations in the rhythmic oscillations of a physiological response pattern in a frequency range of interest. A sensor is used to detect an occurrence of an event in the cycle of a physiological response and the intervals between each reoccurring event is timed and placed in a buffer. The output from the buffer is readout at predetermined time intervals and fed to a filter which determines the aperiodic portion of the signal and subtracts that aperiodic portion to output a residual data signal. The residual data signal is fed to a band pass filter which filters in a region determined by the predetermined frequency range of interest and which outputs to a calculation and display device wherein the variance of the rhythmic oscillation is calculated and displayed.

35 Claims, 8 Drawing Figures

METHOD AND APPARATUS FOR EVALUATING RHYTHMIC OSCILLATIONS IN APERIODIC PHYSIOLOGICAL RESPONSE SYSTEMS

This invention was made with Government support under National Institutes of Health grants Nos. KO2-MH-0054; MH-18909; HD-15968; and HD-05951. The Government has certain rights in this invention.

BACKGROUND OF THE INVENTION

1. Field of the Invention

The present invention relates to the quantification of the variability of physiological activity and particularly the quantification of oscillations in physiological response patterns such as the heart rate.

2. Description of the Prior Art

The measurement and determination of effective diagnostic information from the output of physiological response systems (e.g., heart period patterns, peripheral vasomotor activity, electrodermal potentials, electric potentials from the scalp such as EEGs, blood pressure, temperature and all other physiological activity which may be indexed by time) is complicated by the nature of these response patterns which often are characterized by rhythmic oscillations superimposed on an aperiodic baseline. Extremely complex underlying mechanisms of human physiology underlie the mechanisms which produce the signals. That is, physiological response systems tend not to be determined by a single input but are the result of complex interactions of numerous, often undefined, mechanisms. For example, the nervous system has a profound impact on many physiological responses by modifying "homeostatic" oscillations which represent, in particular circumstances, known physiological mechanisms. More specifically, the heart period (the time between successive heart beats) presents oscillations which are located in frequencies common to other physiological response systems. The heart period oscillates at the breathing frequency and at the frequency at which blood pressure and peripheral vasomotor activity also oscillate. The oscillations in the heart period at the "respiratory" frequency and at the "vasomotor" frequency may be interpreted as an indication of specific physiological mechanisms. (See Sayers, "Analysis of Heart Rate Variability", *Ergonomics,* 1973, Vol. 16, pp. 17–32; and Kitney et al, "Heart Rate Variability in the Assessment of Automatic Diabetic Neuropathy", *Automedica,* 1982, Vol. 4, pp. 155–167.)

When studying the measured physiological activity in terms of oscillations, the parameters of interest in order to provide information of diagnostic value, include the amplitude of the oscillation, the phase of the oscillation relative to other periodic physiological functions at the same frequency and the coupling or coherence between two or more physiological systems at the same frequency. There are numerous methods used to separate the signals of interest or to detrend physiological data. Many of these on-line devices for monitoring the physiological response systems include high-pass, low-pass or bandpass filters. Other methods include specific statistical analysis which have been developed for engineering and economics applications but which are attempted to be used in regard to the detrending of physiological data. In general, most of these prior art procedures assumed that the trend which is being removed may be characterized by a linear regression or the sum of slow sine waves. While these methods appear to function well in some areas of physiological monitoring including respiration and the electrocardiogram, they are rather limited to those instances where the variance associated with the rhythmic oscillations being studied is large relative to the instability of the baseline upon which these oscillations are superimposed. On the other hand, when the variance associated with the oscillations of interest is extremely small relative to the total variance of the physiological response system, then the above assumptions associated with the previous methods and apparatus of detrending do not apply.

An example of an instance where the prior art type of filtering for purposes of detrending the physiological data fails is that of the amplitude of fetal heart rate oscillations which are very small relative to large changes in the heart rate which have been associated with uterine contractions. This is especially pertinent when a compromised hypoxic fetus exhibits massive heart rate shifts in the baseline in response to the uterine contractions, thus making it very difficult to accurately estimate the amplitude of the fast periodic heart rate activity which is of diagnostic value.

Most of the statistical procedures which are used to assess the characteristics of periodic processes such as the amplitude of rhythmic oscillations involve attempts to detrend the baseline to remove aperiodic components from the data set. These periodic processes which are embedded in the complex signal are attempted to be removed through the use of a sequence involving detrending, filtering, and describing the amplitude and periodicity with spectral analysis such as the fast fourier transform (FFT). The detrending and filtering produces a "processed" signal by removing the aperiodic component which allows for the use of statistical procedures to evaluate the amplitude of the rhythmic oscillations. This "processed" signal is decomposed through the use of spectral analysis and the variance is partitioned into constituent frequencies. That is, the variance is described as the sum of sine waves of various amplitudes and frequencies. The problem with this process is that it may result in faulty interpretations of data if the data set being processed violates specific statistical assumptions necessary for proper interpretation.

Spectral analysis may be used to accurately identify and quantify periodic components in physiological response systems when there are only minute baseline shifts or when the baseline trend can be easily removed prior to analysis. Spectral analysis assumes that the data set being analyzed is weakly stationary. A process is weakly stationary, if its mean and variance are independent of time and its autocovariance function depends only on lag (C. Chatfield, *The Analysis of Time Series: Theory and Practice,* Chapman and Hall, 1975). Spectral analysis provides reliable and interpretable estimators of the amplitude of a periodic oscillation only if the data are at least weakly stationary.

Another of the unfortunate physiological response system characteristics is that they are not "stationary". This means that physiological response systems are not perfectly sinusoidal and that they have complex shifts in both the mean level and the variance. Thus, by their nature, they violate the assumption of stationarity. Quite obviously then, the spectral analysis to evaluate the amplitude of rhythmic oscillations will result in unreliable estimates of the amplitudes of the rhythmic process at any specific frequency band. By appropriately removing the complex baseline trend, it would be possible for the amplitude of the periodic oscillations to be accurately measured in the filtered data set; however, all of the existing filtering methods and devices which have been used to "detrend" physiological response activity in order to remove the shifting baseline have made faulty assumptions.

Many existing physiological monitoring devices such as polygraphs, electroencephalographs, and electromyographs have hardware filters which function as high-pass, low-pass, or bandpass filters. As previously discussed, this reflects an assumption that there are no aperiodic components in the data and merely that the filters pass the frequency band of interest to the output. Unfortunately, since the data of most physiological systems contain aperiodic trends, the amplitude of the frequencies passed by the various filters will be partially a function of the amount of variance passed through the filters which is, in reality, a portion of the complex aperiodic trend discussed above. Thus, in essence, the hardware filters of prior art devices assume that the baselines are merely the sum of slow sine waves and a linear trend. If the trend is complex and cannot be described by a linear regression or a sum of sine waves with known periodicities and amplitudes, then the sine waves necessary to describe the slow complex trend may include faster periodicities superimposed on the frequencies of interest. Therefore, the operators of the device must know beforehand the shape of the trend to be subtracted from the data set. In the case of spectral analysis, it would be necessary to subtract the spectral densities associated with the trend from the spectral densities associated with the total data set. This is totally impractical because, with the filters being used, the operator would never be able to separate what component of the variance being passed by the filter is associated with the trend from that component of the variance which would be associated with the periodic process. Moreover, it would preclude the ability of the operator to monitor the changing conditions of the periodic physiological process in an on-line operation.

Other methods of operating a filter for removing trends include the use of what is called "successive differencing". This method consists of successively subtracting values through the entire data set involving, for example, the subtraction of data point number 1 from data point number 2 and data number 2 from data point 3, etc. Due to the transfer function of this filter the method may result in an underestimate or overestimate of the spectral densities depending on which frequencies are of interest to the investigator and thus may result in a contamination of the estimates of the variance at any specific frequency. Moreover, the "successive difference" filter is similar to linear detrending and suffers from the same problem of passing variances in higher frequency bands which are components of the aperiodic trend. Other methods include low order polynomial detrending techniques which do not succeed in removing the trend and which also result in an alteration in the shape of the spectrum by influencing both the identification of the peak frequency and the estimate of amplitude at a given frequency.

The clinical and diagnostic value of overcoming the errors brought about by incorrect or simplified assumptions in the prior art devices discussed above can be particularly seen in a specific situation where the amplitude of the oscillation of a physiological process may serve as an indexing variable of a specific underlying mechanism. For example, in the case of heart period, it is possible to interpret the amplitude of the oscillation of heart period at the respiratory frequencies or respiratory sinus arrhythmia (RSA) as an index of the influence of the vagus (10th cranial nerve) on the heart. Briefly stated, the respiratory system transmits afferent information to the brainstem where it "gates" (turns off and on) the vagal efferents to the heart (i.e., vagal efferent activity is reduced during inhalation and reinstated during exhalation). Thus, with regard to heart period oscillations occurring in the respiratory frequencies, the amplitude of such heart period oscillations conveys information regarding the "vagal tone" effect on the heart. With regard to clinical and diagnostic relevance, higher order central nervous system disorders such as intracranial hemorrhage result in a decrease in the vagal efferent influence on the heart. Therefore, the amplitude of the heart period oscillation in the respiratory frequency band (RSA) may provide a "window to the brain" and an early assessment screening of the central nervous system dysfunction.

One of the more important points concerning the relationship exhibited by a fetal heart period is that the heart period pattern exhibits small oscillations at the periodicities associated with breathing in the newborn which frequencies are most likely representative of the RSA in the fetus. Because the periodicities may account for much less than one percent of the total variance of the heart period pattern, the above-discussed points with regard to prior art methods of evaluating and detecting the amplitude of the periodic function become more critical and more prone to error because the percent of variance that the specific periodic function accounts for is extremely small relative to the total variance of the physiological response pattern in the fetal heart period.

In the fetus, the heart period is mainly influenced by the feto-maternal movement and the impact of uterine contractions during labor. Spectral analysis of fetal heart period utilizing any one of the above-discussed filtering techniques would mask the presence of the small oscillations because the percent of variance would be so low that it would not result in a significant or even recognizable peak in the spectrum and because the variance from the complex trends related to either feto-maternal movement or uterine contractions would produce more variance in the frequency band of RSA than the RSA itself.

In summation then, the spectral analysis provides interpretable estimates of the variance (amplitude) on specific frequency bands only when the data do not violate specific assumptions. Most data sets derived from physiological systems such as heart period activity contain aperiodic components and violate the critical assumption of weak stationarity (i.e., the mean and variance are independent of time and the autocovariance function depends only on lag). This is critical when the amplitude of the oscillations of periodic physiological activity conveys critical information regarding the condition of the organism as the instance when the reduction in the amplitude of RSA in the human neonate is associated with brain damage and/or nervous system conditions threatening the viability of the infant. Likewise, spectral analysis and most of the filtering techniques which attempt to remove the trends, are not readily adapted for rapid on-line use.

SUMMARY OF THE INVENTION

It is a primary object of the present invention to provide a device which incorporates a filtering system which "on-line" removes the variance associated with complex trends and slow sine waves enabling accurate estimates of more rapid periodic oscillations when they are superimposed on complex trends and slow sinusoids.

It is also an object of the present invention to incorporate a procedure which provides an accurate evaluation of the amplitude of a rhythmic oscillation on a frequency band when the rhythmic oscillation is superimposed on an aperiodic response pattern. The procedure involves the removal of the effect of baseline drift by detrending the baseline activity with a "moving polynomial filter" (MPF). The moving polynomial filter consists of two stages: first, it smooths the baseline pattern by fitting a piece-wise polynomial to the baseline; second the smoothed baseline pattern is subtracted from the original data set. The residuals represent a filtered data set with a low frequency cutoff. The output of this procedure is then bandpassed to allow only the variance of the data set associated with the frequency of interest to pass. The output of these two filtering devices and methods provides the component of variance associated with rhythmic oscillation of interest.

It is also an object of the present invention to provide a moving polynomial filter (MPF) which provides an ability to assess on-line the continuous shifting amplitude of the oscillation of interest during situations when the periodic process being monitored is not weakly stationary and which functions to assess the amplitude of oscillations on-line without the collection of data for an entire session prior to detrending.

It is also an object of the present invention to provide an apparatus and method for detecting central nervous system dysfunction in humans by providing an arrangement of detectors and filters which output a clinically usable signal providing an indication of disorders in the central nervous system through the monitoring of the heart rate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings where:

FIG. 1b is a representation of the smoothed baseline template to be removed from FIG. 1a.

FIG. 1c is the residual from resulting subtracting of the template of FIG. 1b from the pattern FIG. 1a.

DESCRIPTION OF THE PREFERRED EMBODIMENTS

Figure 1A:
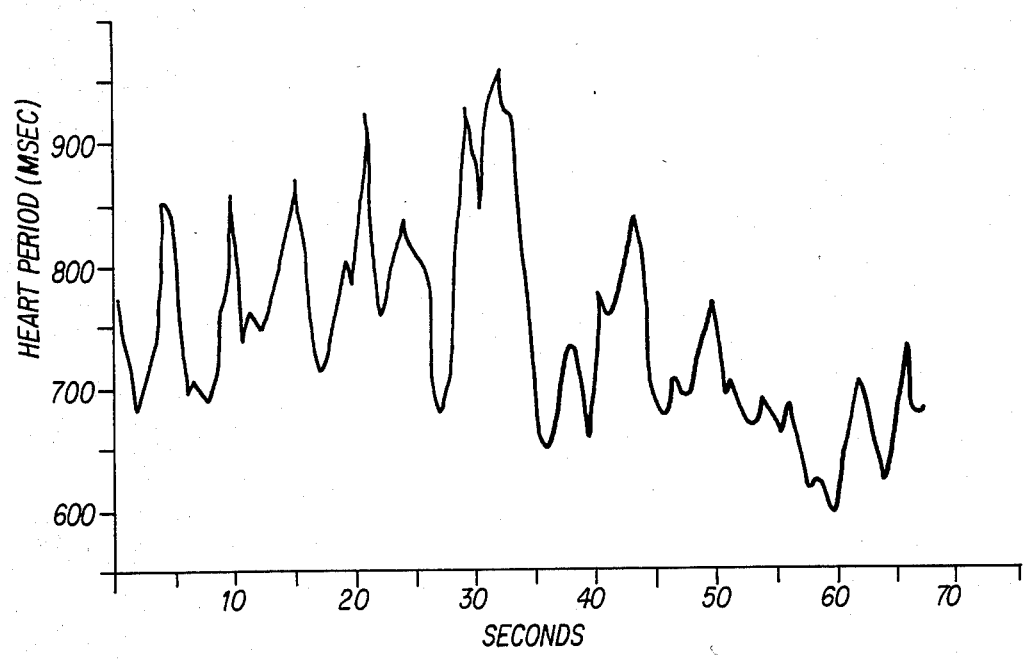
FIG. 1a is a representation of a physiological response pattern characterized by with a rhythmic oscillation superimposed on an aperiodic response pattern.

Referring now to the drawings, wherein like reference numerals designate identical or corresponding parts throughout the several views, and more particularly to FIG. 1a thereof, there is shown a superimposition of the amplitude of a rhythmic oscillation of a known frequency band on an aperiodic response pattern. This complex signal serves as a model for physiological response patterns.

A specific example of the type of complex system illustrated in FIG. 1a is that associated with the oscillation of heart period which must be "separated" in order to provide the measurement of the vagal tone which, as previously discussed, is the spectral representation of the amplitude of periodic heart period activity associated with the "gating" by respiratory activity of the vagal efferents to the heart. The accumulation of spectral density estimates of heart period activity associated with the respiratory frequency band provides an accurate measurement of respiratory sinus arrhythmia (RSA). The vagal tone, as measured by the amplitude of the RSA, provides a key to the link between the heart rate response and an underlying physiological dysfunction. More particularly, the amplitude of the RSA may be employed as an index of central nervous system dysfunction or influence.

In order to provide clinically reliable information for use as a diagnostic tool, the rhythmic oscillation of FIG. 1a must be separated from the underlying aperiodic signal.

Thus, if the heart period activity is filtered to pass only the frequencies associated with respiration, the new heart period series would represent the RSA. Because the amplitude of any sinusoid is monotonically related to its variance, the amplitude of the sinusoid resulting from the bandpass filtered heart period activity would represent a sort of breath-by-breath RSA. An instantaneous estimate of the vagal tone could be derived by linear interpolation connecting the peaks of the adjacent filtered heart period oscillations.

In physiological response patterns, non-sinusoidal processes distort the estimates of the underlying rhythmic processes. Thus, it is necessary to remove these aperiodic influences prior to estimating the variance or amplitude associated with specific rhythmic processes. Generally, the methods used to detrend the baseline drift have assumed that aperiodic influences may be removed by detrending with a linear regression or fitting the entire data set to a low-order polynomial. However, most baseline trends in physiological response patterns are aperiodic so that neither a polynomial fit nor a sum of slow sine waves can adequately represent the trend. For example, in the human fetus, there is a relatively fast frequency (25 to 75 cycles per minute) in the fluctuation of the heart period pattern. This pattern is difficult to evaluate because it may be superimposed on slower shifts in the heart period. One source of the slow shifts is the mother's uterine contractions. Thus, the rhythmicity of the fetal heart period pattern, which at specific times is stationary, is superimposed on a slow complex trend.

Figure 1B:
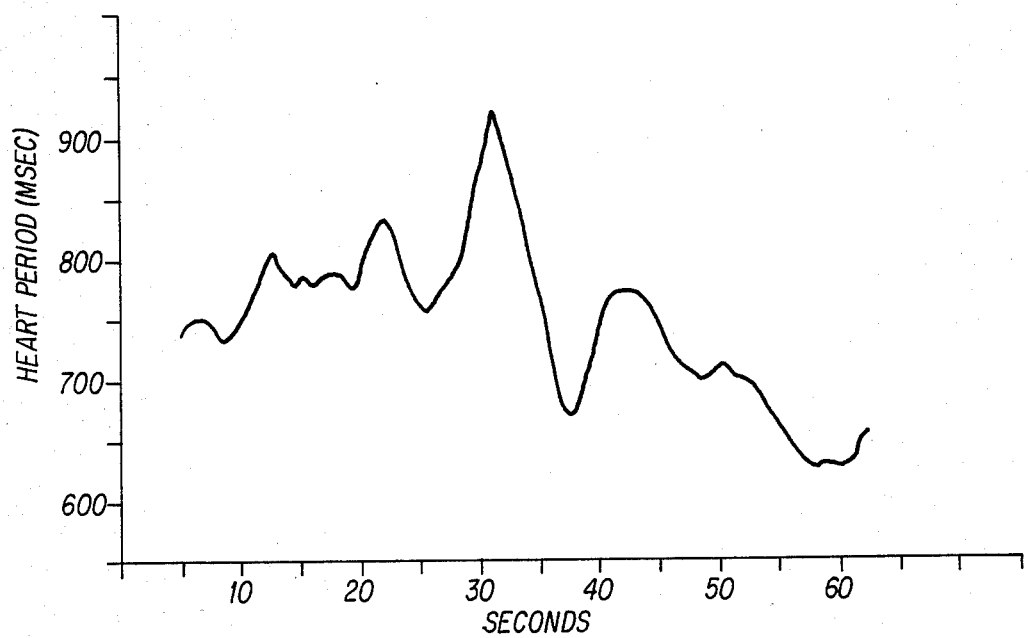

The complex trend in the fetal heart period pattern as related to the uterine contractions cannot be removed by linear detrending nor by detrending low-order polynomials. However, a local cubic polynomial moving average may be stepped through the data to produce the desired series. The moving average is a weighted sum applied locally along the curve to obtain a smooth curve or template as shown in FIG. 1b. This template of slow activity is then subtracted from the raw data and the residual series of FIG. 1c contains the rhythmic process which is free from the influences of the aperiodic component and is stationary over short segments. In the case of the fetal heart period pattern, the residuals are a time series consisting of the fast fluctuations. These fast fluctuations may not be stationary over long periods of time, because the amplitude of the oscillations may change as the condition of the fetus's central nervous system changes.

Figure 1C:
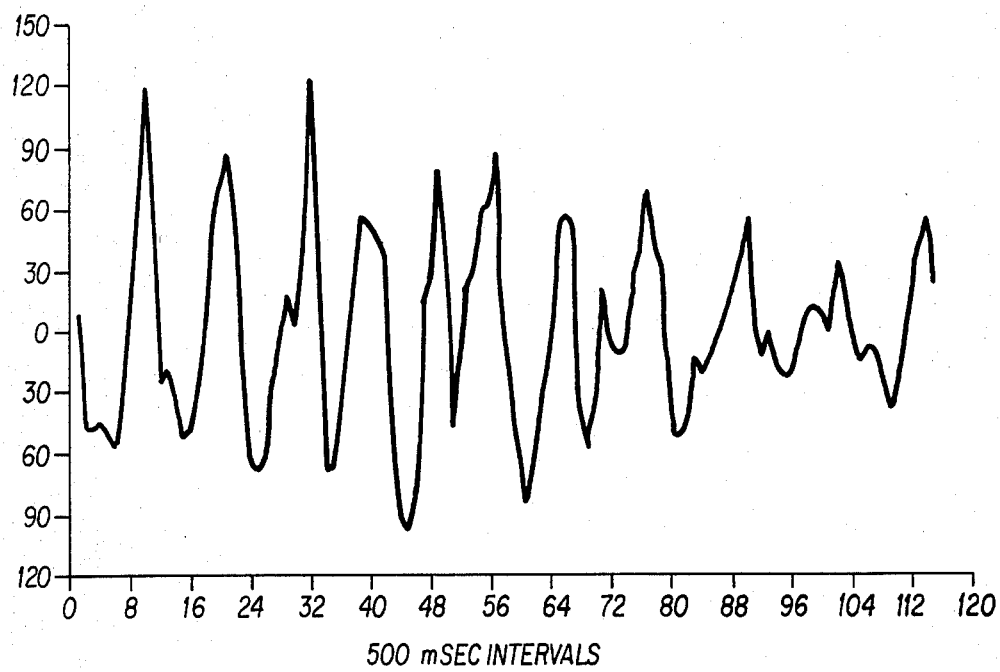
Figure 2A:
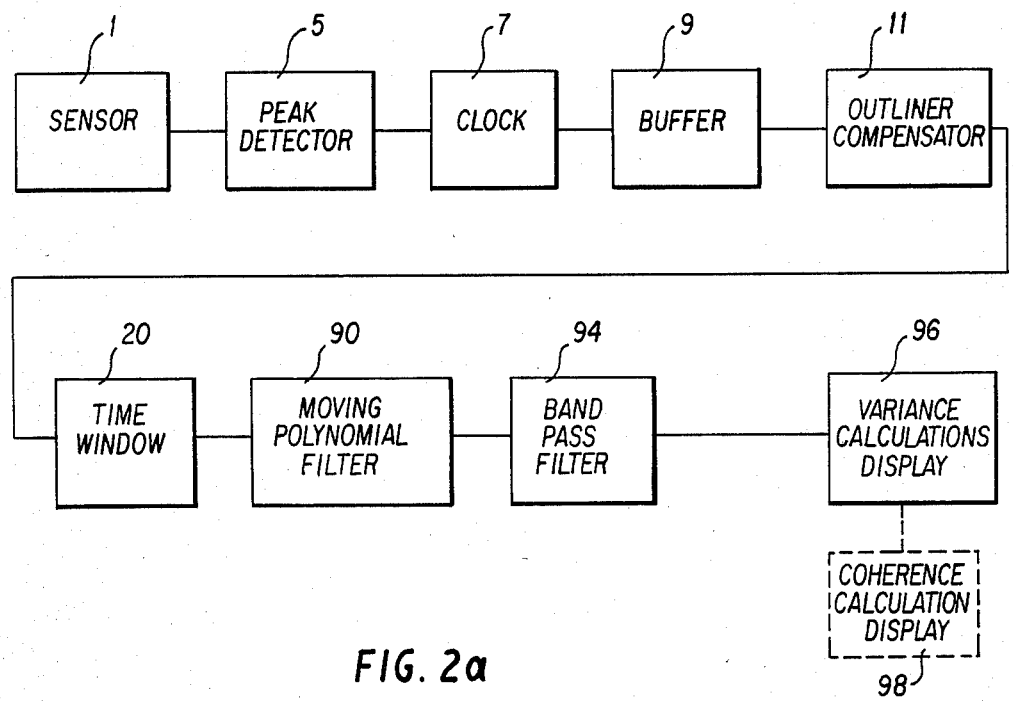
FIG. 2 is a block diagram of the device for evaluating the amplitude of the rhythmic oscillations superimposed on the aperiodic response patterns.
Figure 2B:
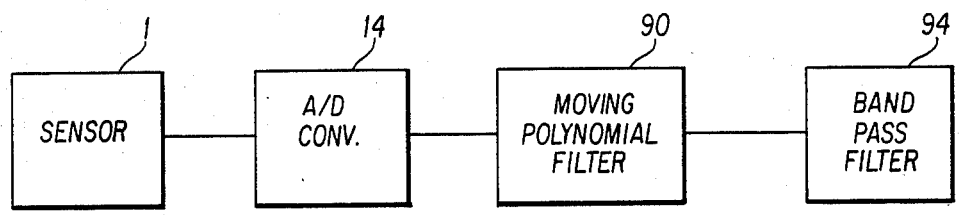

The FIG. 2a, 2b details an apparatus which functions to remove the rhythmic oscillation of interest from a physiological response pattern as shown in FIG. 1a, 1b, 1c. The sensors 1 are provided by pickups which sense physiological activity from the body to include electrodes to detect endogeneous bioelectric potential as the beating of the heart in an EKG as well as the volumetric and plethysmographic sensors to assess response systems such as respiration and blood flow. The output from the sensors may be either seen to be a point process (FIG. 2a) which is manifested as events in time such as the beating of the heart or a continuous process (FIG. 2b) which is manifested as continuous changes over time such as the changing of the circumference of the chest during respiration and the electrical potential of the finger or scalp. In using a measurement of a point process as shown in FIG. 2a, the component of the sensor device which is called the "event or peak detector" 5 detects the time of occurrence of specific events in a point process. In the instance of heart periods this could be the detecting of an occurrence of a R-wave in the EKG representing the contraction of the ventricles of the heart. The occurrence of the peak of the R-wave is detected with an accuracy of one msec with a pattern recognition algorithm. The output of the peak detector is fed to a clock 7 which times the intervals between successive events in msec.

The values of the clock are stored in a buffer 9 for later use and the output of this buffer 9 is fed to an outlier compensator 11 which monitors the timing between events of interest such as the occurrence of the R-waves. The compensator contains information concerning the expected range of time intervals between the R waves based upon a knowlege of the subject being tested. This outlier compensator maintains a specific interval between event occurrences which are later to be analyzed by the remainder of the circuitry.

Some of the problem overcome by the outlier compensator include the problem which occurs with regard to specific ventricular arrhythmias which result in an out-of-place event detection. For example, ventricular extrasystoles are followed by a compensatory pause. Ventricular extrasystoles do not interrupt the regular discharge of the sinoatrial node. The duration of the beat with the ventricular extrasystole plus the beat following with the compensatory pause are equivalent to the duration of 2 normal beats. Of importance is the fact that centrally mediated rhythms, such as RSA, which are manifested in the heart period pattern are naturally occurring arrhythmias of the sinoatrial node. Ventricular extrasystoles do not interrupt or influence these rhythms. Thus, to provide an accurate estimate of the variances associated with heart period rhythms such as RSA, it is necessary to correct for ventricular extrasystoles and compensatory pauses. The outlier compensator would adjust for the ventricular extrasystole and compensatory pause by adding the two time periods together and dividing by two. Thus the outlier compensator is no more than an adder and a divider circuit arrangement programmed to operate when the duration between events fed from the buffer 9 is outside of a range of expected event intervals based upon the subject being tested. In this instance, the outlier compensator removes this event by adjusting the space between the events in accordance with its expected spacing interval. Other areas where the outlier compensator 11 is functionally important include the instance where there is a missing beat due to the failure of the components of the "event detector" to be triggered or in the instance where it is triggered prematurely resulting in too many beats. In each of these instances the outlier compensator checks and maintains a proper predetermined interval range between the beats by either adding together the intervals or dividing an interval by two.

The output from the compensator is fed to the time window 20. This time window 20 measures the time interval between the event being detected such as the R-wave within a specific time frame or window. For example, if a time window operates every 500 msec then the data set is transformed into an estimation of heart period for each 500 msec time window and is outputted to the moving polynomial filter 90. The determination of the time interval is in cooperation with the frequency characteristics of the underlying process and the moving polynomial filter 90. The timing or the duration of the time window is critical to prevent aliasing. As is known in the art of signal processing aliasing occurs when there are variances associated with frequencies which are faster than those frequencies being detected and those variances from outside the frequency band of interest are folded back (i.e., added to) onto those frequencies of interest. In order to protect against this aliasing in the heart rate example the time window is set to be such that the time window samples are approximately twice as fast as the R-wave events which identify each heartbeat. Thus if the normal heart rate is assumed to be 60 beats per minute the sample or time window is set at twice the speed or 2 events per second. In other words, the window operates every 500 msec to dump its data output to the filter. The use of a sampling rate set at twice the frequency of interest is based upon a statistical rule set down by Blackman and Tukey (R. B. Blackman & J. W. Tukey, *The Measurement of Power Spectra*, 1959, New York: Dover) which basically realizes that if the sampling is twice as fast as the event in being detected it is sufficient to provide all of the details of the event without any aliasing from frequencies not of interest. In other words it prevents the folding back phenomena. Quite obviously the time window could be set to smaller intervals (i.e., faster sampling rate) as long as it obeys the basic rule of sampling at at least twice the frequency of the event of interest.

To adequately employ a moving polynomial filter (MPF), the data must be sampled at appropriate time intervals. Since the moving polynomial filter (MPF) functions in the time domain and assumes that the data are sampled at equal time intervals, it is important that those of the processes which are called "continuous processes" must be sampled at a rate to generate discrete processes containing the variance associated with the fastest oscillations in the process. The choice of the sampling interval is critical because it is not possible to identify rhythms whose period is less than twice the time between observations. It can be mathematically demonstrated that faster frequencies (i.e., faster than twice the duration of the sampling interval) will be "folded back" or "aliased" on the slower frequencies. This may result in an overestimate of variances in the frequency band of interest (P. Bloomfield, *Fourier Analysis of Time Series: An Introduction*, Wiley, 1976). The FIG. 2b details the apparatus necessary for a continuous process wherein the same numbers represent identical apparatus in FIG. 2a. Basically, the Analog-to-Digital (A/D) converter 14 is used instead of the Peak detector 5, the clock 7, the Buffer 9, the compensator 11 and the time window 20 due to the above discussed nature of a continuous process. The sampling rate of the A/D converter 14 is analogous to the time window 20 of the Point Process because of the need to sample a "Continuous Process" at a rate so that the variance associated with the fastest oscillations are contained in the "discrete processes" from the A/D converter 14. It also should be noted that continuous processes must be sampled at equal time intervals while point processes described by interevent time intervals (e.g., heart period: the time between successive heartbeats) must be transformed by appropriate weighting or sampling into equal time intervals. The prior art does not provide for filtering point processes in the time domain. Accordingly, the device of the present invention transforms the point process to a discrete process sampled at equal time intervals. This enables the application of time domain filters to point processes. With regard to continuous processes, it is necessary to have prior knowledge of the physiological system being evaluated. If it is not known what the periodic components embedded in the physiological process are, aliasing may result in the estimates of variance being uninterpretable. The moving polynomial filter (MPF) provides furthermore a facilitation in the ability to assess the amplitude of oscillations on-line because it does not necessitate the collection of data for the entire session prior to detrending. The MPF also functions in situations in which the rhythmic process being studied is not stationary and provides the ability to assess on-line the continuous shifting amplitude of the oscillation of interest.

The moving polynomial filter functions as a high-pass filter when the smooth template is subtracted from the data set. The frequencies passed by the filter are a function of the duration of the polynomial which is defined by the number of data points incorporated into the moving polynomial with each data point representing a time-sampled measure. In physiological applications a third order polynomial is most appropriate because it enables the removal of cubic dips in the trend.

The moving polynomial filter 90 which is fed with the time windowed data set includes a digital filter which is stepped through the data set. A low order polynomial is fit on a "local" level to describe the aperiodic trend. Although a polynomial fit of trend over the entire data set suffers from many practical and statistical problems, any smooth function can, under very general conditions, be represented locally by a polynomial to a fairly high degree of accuracy. By stepping a localized polynomial through the data, it is possible to smooth the data set and to describe the complex aperiodic trend. When the "smoothed" trend is subtracted from the original data, the residuals represent a filtered data set which contains accurate representations of the faster rhythmic activity uncontaminated by the complex aperiodic processes.

A polynomial is fit to the first $2m+1$ data points to determine the "trend" value at data point $m+1$ (i.e., the middle of the range of the data points which are fit with the polynomial). To determine the trend value at data point $m+2$ the same order polynomial is fit to another $2m+1$ data points moved one time point forward. This process is continued through the data set until the polynomial is fit to the last $2m+1$ data points. The filter is created when the trend values determined by the moving polynomial are subtracted from the original data. Thus, the name "moving polynomial filter". Note that $m$ data points at the beginning and end of the data set are forfeited. Since the procedure is equivalent to taking linear combinations of observations of physiological activity with coefficients, the coefficients need to be calculated only once for a polynomial of a specified order and number of points and the coefficients may be used in all subsequent applications (see M. G. Kendall, *Time Series*, 1973, Griffin).

The cubic polynomial may be expressed in the general form: $a_0 + a_1 t + a_2 t^2 + a_3 t^3$ where t is time and the constants "a" are determined by the principle of least squares to minimize $$\sum_{t=-m}^{m} (Y_t - a_0 - a_1 t - a_2 t^2 - a_3 t^3)^2$$

where $Y_t$ represents the raw untransformed data point at time t, m is the number of time windows on each side of the midpoint of the polynomial. In our 21 point example, m would be ten 500 msec time windows on each side of the midpoint. Since we are only interested in generating a transformed "trend" value at time $t=0$ (i.e., the midpoint of the polynomial) using the information of $-m$ and $+m$ data points, we need solve only for $a_o$ which represents the weighting coefficients to be applied to each of the $2m+1$ data points to produce the best cubic polynomial fit, i.e., the least squares difference between the raw data and the smoothed "trend" at time $t=0$. Note that $a_O$ is a set of weighting coefficients, one for each of the $2m+1$ data points. Through a series of mathematical calculations the constant $a_O$ is calculated for a specific polynomial defined by a given order, n, and number of points, $2m+1$ M. G. Kendall in chapter 3 of *Time Series*, 1973, Griffin, provides the mathematical examples for calculating the set of coefficients defining "$a_O$". The generalized expression to minimize the least squares difference for any polynomial of order n and number of time points $2m+1$ is presented below.

$$\sum_{t-m}^{m} (Y_t - a_0 - a_1 t - \ldots a_n t^n)^2$$

The moving polynomial has two important properties. First, the weights of the coefficients sum to unity. This is easily seen if the coefficients are applied to a series consisting simply of a constant which is repeated, since the average must be that same constant. Second, the weights are symmetric about the middle value.

As stated above, the weighting coefficients used in the moving polynomial filter, are those which minimize the least squares difference between the "real" observed data set, $Y_t$, and the polynomial of order "n" and $2m+1$ data points. In the above example, $n=3$ (i.e., cubic) and $2m+1=21$. Once the weighting coefficients are calculated for a polynomial fit on any data set (real or hypothetical) it is not necessary to generate new coefficients.

The following is a computer program which generates the coefficients for any polynomial of 5th order or lower with no limitations on the number of points.

```
PROGRAM TRY(INPUT,OUTPUT)
DIMENSION A(100)
READ *,N1,N2
CALL POLMOV (N1,N2,A)
PRINT 50, (A(I),I=1,N2)
50 FORMAT (10F8.5)
STOP
END
SUBROUTINE POLMOV (N1,N2,A)
COMPUTES MOVING POLYNOMIAL FILTER
COEFFICIENTS FOR C POLYNOMIALS OF
DEGREE N1 (2 .LE. N1 .LE. 5) BASED C ON A TOTAL
OF N2 POINTS.
DIMENSION A(N2)
IF(N1.LT.2 .OR. N1.GT.5) RETURN
IF(N1+1 .GT. N2) RETURN
IF(2*(N2/2) .EQ. N2) N2=N2−1
N3=N2/2
A0=N2
A2=0.
A4=0.
A6=0.
A8=0.
DO 1 I=1,N3
AI=I
A2=A2+2.*AI**2
A4=A4+2.*AI**4
A6=A6+2.*AI**6
1 A8=A8+2.*AI**8
IF(N1 .GT. 3) GOTO 45
AJ=−N3−1
DEN=A0*A4−A2*A2
DEN=1./DEN
DO 2 I=1,N2
AJ=AJ+1.
AJ2=AJ*AJ
2 A(I)=DEN*(A4−AJ2*A2)
RETURN
DEN=
A0*A4*A8+2.*A2*A4*A5−A6**3−A0*A6*A6−A2*A2*A8
DEN=1./DEN
C1=A4*A8−A6*A6
C2=A4*A6−A2*A8
C3=A2*A6−A4*A4
AJ=−N3−1
DO 3 I=1,N2
AJ=AJ+1.
3A(I)=DEN*(C1+C2*AJ*AJ+C3*AJ**4)
RETURN
END
```

Examples are provided for 7, 21 and 35, point polynomials of the third order. Note that the sum of the coefficients approximate unity. They do not exactly sum to one since the computer approximates a fraction as a decimal.

Figure 3:
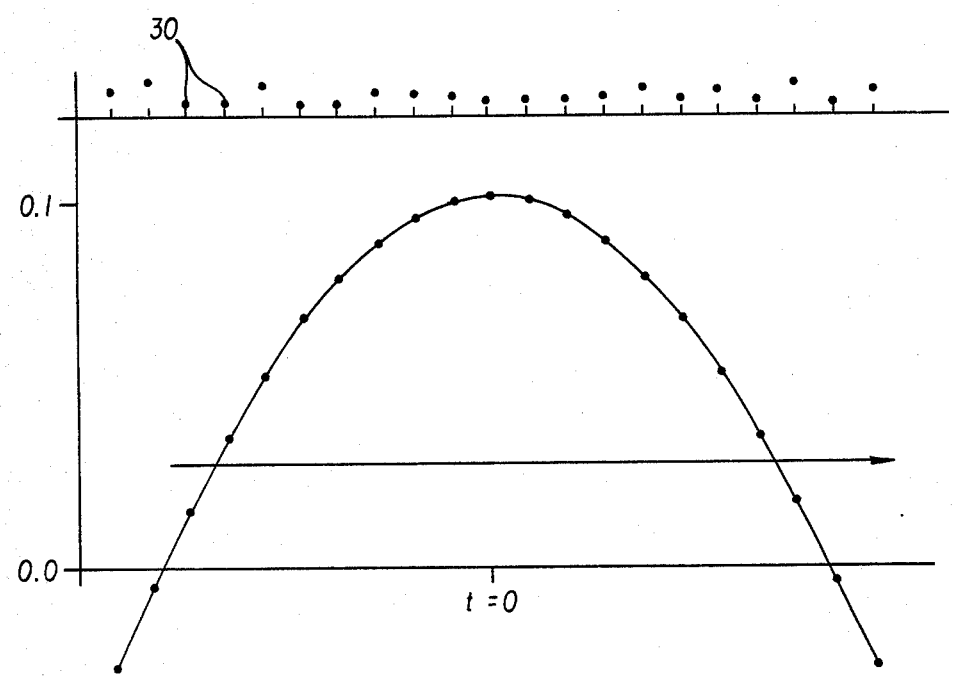
FIG. 3 is a graphic illustration of the moving polynomial filter of FIG. 2.

FIG. 3 shows a graphical representation of the moving polynomial filter as it acts on the data sets 30 output from the time window 20 of FIG. 2a. The filter 90 of FIG. 2 is constructed so as to present to the data 30 a set of 21 coefficients derived from a least squares cubic polynomial fit. The coefficients for each of 21 (2m+1) points are plotted in the curve shown in the FIG. 3. Thus the actual construction of the curve shown in the FIG. 3.

Once the coefficients have been calculated the data set is multiplied by its corresponding calculated coefficients to produce a template which is the smoothed trend as shown in FIG. 1B. The template of signals is then substracted from the original data set of FIG. 1A which includes the data set outputs from the time window in order to obtain the signal shown in FIG. 1C as an output from the moving polynomial filter. The value for the template associated with point 11 is determined by multiplying each of the points 1 through 21 by its corresponding normalized coefficient and adding the values together to obtain the value for the template point corresponding to the point 11. It is to be noted that because the polynomial coefficients sum to unity the normalization is automatically taken into account so that the value for the smooth template which corresponds to the raw data point 11 is obtained by merely adding together all of the multiplied values of the raw data points 1 through 21 with their corresponding coeffients from the curve. After the summation has taken place to establish a corresponding template point for the raw data point 11 then the filter, so to speak, moves to data point 12 and the calculation for the data point 12 is determined by multiplying the values of the data points 2 through 22 by the corresponding coefficients which are now centered at data point 12. Thus the nomenclature "moving polynomial." It can also be seen that if a 21 point polynomial filter is used then there is no calculation for the points 1 through 10 nor for the last 10 points of the data set because the calculation for each particular point of raw data requires 10 information points from the past and 10 information points from the future data points. The construction of a filtering device in accordance with the generalized polynomial equation and its corresponding calculated coefficients based upon the number of data points can be a hardware implementation once the values of the coefficients are determined, since they are constants for polynomials of a specific order and number of points.

One of the key areas in this polynomial filter which provides for a passage of useful information is the choosing of the number of data points which are to be fit by the polynomial. For instance in the heart rate embodiment if the respiration frequency which is the

| 3rd order. 7 points | | | | | | |
|---|---|---|---|---|---|---|
| −.09524 | .14286 | .28571 | .33333 | .28571 | .14286 | −.09524 |
| 3rd order. 35 points | | | | | | |
| −.03707 | −.02548 | −.01460 | −.00442 | .00505 | .01383 | .02190 |
| .02927 | .03594 | .04191 | | | | |
| .04717 | .05174 | .05560 | .05876 | .06121 | .06297 | .06402 |
| .06437 | .06402 | .06297 | .06121 | .05876 | .05560 | .05174 |
| .04717 | .04191 | .03594 | .02927 | .02190 | .01383 | .00505 |
| −.00442 | −.01460 | −.02548 | −.03707 | | | |
| 3rd order. 21 points | | | | | | |
| −.05590 | −.02484 | .00294 | .02746 | .04871 | .06669 | .08140 |
| .09284 | .10101 | .10592 | .10755 | .10592 | .10101 | .09284 |
| .08140 | .06669 | .04871 | .02746 | .00294 | −.02484 | −.05590 | frequency of interest with regard to its effect on the heart rate is approximately 0.25 Hertz or a breath every 4 seconds, then in order to insure that the variance of the breathing process of interest is passed unattenuated the "twice duration rule" comes into effect. This rule basically states that in order to deal with both the shape of the transfer function of the filter which determines the shape of the frequency cut-off of the filter and the fact that the frequency of physiological processes are not constant but vary within a predictable range the use of a polynomial having a duration fitted locally at approximately twice the modal duration of the periodic process being studied insures that the variance of the periodic process of interest in is passed unattenuated or unembellished. Using this rule then the time duration of the polynomial filter necessary to insure the passage of all points of interest in a respiratory frequency band which is characterized by a modal breathing frequency of 15 breaths per minute is 8 seconds. The breathing frquency may not be constant at 0.25 Hz but may vary from approximately 0.15–0.40 Hertz. The modal frequency (i.e., dominant periodicity) may vary among subjects, but most adults breathe with a modal frequency between 0.15 and 0.40. Therefore, it can be seen that a 21 point polynomial filter generally satisfies this requirement as each point taken from the time window is separated by 500 msec and therefore the 21 points encompass a time frame of 10.5 seconds which is sufficient to pass those events of interest occurring because of the respiration. It should also be noted that in some instances depending upon the application of the filtering device it is not advantageous to increase the number of points too broadly because this would effectively pass the variance associated with slower periodic and aperiodic processes. Since physiological processes are not perfect sine waves, passing lower frequency physiological activity will always result in the passing of higher frequency harmonics which may be superimposed on the variance of the frequency band of interest.

The selection of the cubic order for the polynomial considerably enhances the ability of the filter to respond to and "fit" cubic trends. Higher order polynomials may, on the local level, start to map into the faster periodic activity, while lower order polynomials may not "bend" with the baseline trend. In summation then, the cubic order polynomial is chosen because it maps the dips in the response pattern without mapping into the faster periodic component.

A bandpass filter 94 is added to the output of the MPF in order to reduce the output variance to only periodicities of interest. This necessitates prior knowledge of the physiological rhythms which are being studied. For instance, with regard to respiratory sinus arrhythmia (RSA), it is determined by the natural range of breathing for the age for the human being tested. The output of the bandpass filter is equivalent to the variance of the frequency band of interest and is output to a variance calculator and Display 96. Because all physiological oscillations are not perfect sine waves, the periodicities are manifested across a band of frequencies. Thus, the sum of the variances associated with this band of frequencies is desired. This sum may be calculated per time period with spectral analysis and by summing the spectral densities associated with the frequencies of interest. Likewise, in situations in which rapid and continuous estimates are required, the variance may be calculated with traditional descriptive statistics from the output of the bandpass filter. When the rhythmic oscillation in heart period is clearly distinguished from the background activity through the above processes, the variance which is calculated by either of the above two methods provides an estimate of the vagal tone.

In the above analysis the bandpass filter 94 which takes the output of the MPF passes only the frequencies of interest which in the case of RSA with adults requires a bandpass of 0.15–0.40 cycles per second in order to allow only the periodicities associated with breathing to pass.

When the coupling of two or more physiological processes needs to be evaluated, the simultaneous output of two series fed through the filtering procedure may be analyzed with cross-spectral analysis and a weighted coherence may be calculated. This is shown in FIG. 2 as block 98. Since the weighted coherence (see Porges ete al., "New time-series statistic for detecting rhythmic co-occurrence in the frequency domain: The weighted coherence and its application to psychophysiological research," *Psychological Bulletin*, 1980, 88, 580–587) is derived by weighting the coherence function across a band of frequencies by the spectral densities, accurate estimates of the spectral densities provided by the above procedures are necessary to generate an appropriate estimate of the weighted coherence.

Figure 4A:
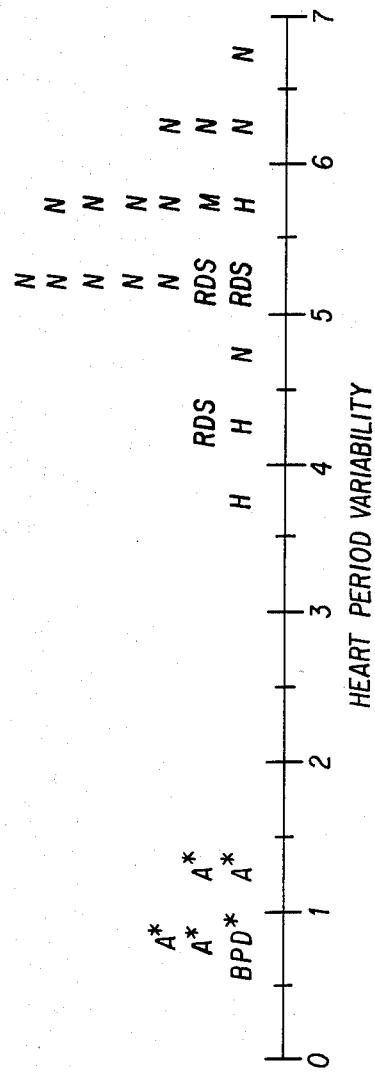
FIG. 4 is an illustration of the clinical importance of the method and apparatus of the present invention of FIG. 2.
Figure 4B:
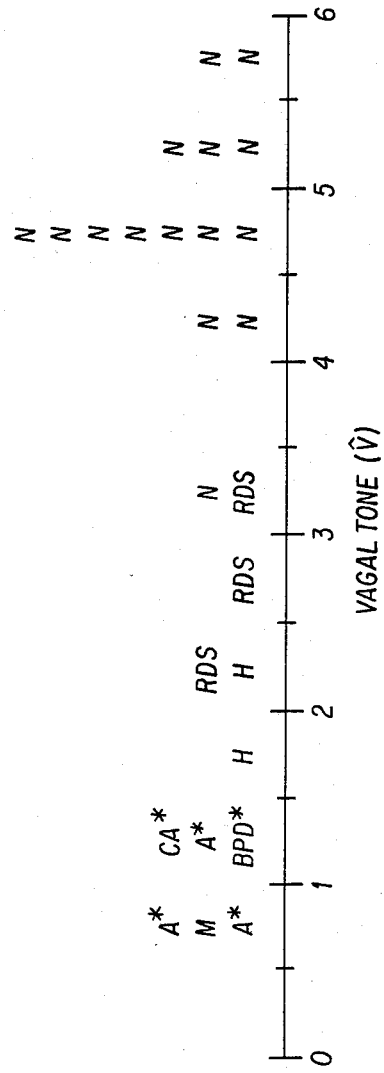

The FIGS. 4a,b shows a clinical application of the results of the analysis detailed above by the structure of FIG. 2. The detection and evaluation of the component of the heart rate pattern which is directly influenced by the central nervous system, called the vagal tone, is detected by the output of the FIG. 2. An evaluation of the vagal tone in a group of normal infants and a group containing a variety of clinical pathologies including severe brain damage is detailed in the FIG. 4b. The total heart period variability was also collected. There is an apparent monotonic relationship between the vagal tone detected by the embodiment employing the structure of FIG. 3 and the severity of clinical dysfunction. When the same infants were ranked in terms of their heart period variability as in FIG. 4a, there was a clear distinction only between those who died and all other infants. While heart period variability clearly distinguished between brain death infants, with their characteristic absence of neural influence on the heart, and all other infants, it did not distinguish among the various infants having neural tube defects, respiratory distress syndrome, and normal infants. The letters on the Scale of FIGS. 4a,b represent the diagnosis or insult associated with individual infants (A=asphyxia; BPD=bronchio-pulmonary dysplasia; CA=cardiac arrest; H=hydrocephalic; M=microcephalic; N=normal; RDS=respiratory-distress syndrome; *=denotes infants who subsequently expired). Heart period did not reliably discriminate among the various pathologies although there was a tendency among the severely brain damaged to have short heart periods. Categorization with the heart period variability of FIG. 4a partitioned the infants into two global categories while classification by vagal tone in FIG. 4b as measured with the FIG. 2 embodiment allowed for a continuum of severity of neuropathology. Thus, although the heart period variability of FIG. 4a, which was used previously as an indicator in this type of diagnosis, is sensitive to gross dysfunction, it is quite clear that the vagal tone used in FIG. 4b is a more sensitive index to individual differences in central dysfunction.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A system for detecting amplitude variations in the rhythmic oscillations of heart period in a predetermined frequency band of interest, comprising:
   sensor means for detecting an occurrence of an event in the cycle of a heartbeat;
   timing means for determining time intervals between the occurrence of said event in successive heartbeats;
   buffer means for storing said time intervals between the occurrence of said event in successive heartbeats;
   means for reading out said intervals stored in said buffer means at predetermined time intervals;
   first filter means responsive to the intervals read out from said buffer means, including a means for determining an aperiodic portion of said intervals read out from said buffer means and a subtraction means for subtracting said aperiodic portion from said intervals read out from said buffer means and for producing a corresponding output;
   second filter means for receiving and filtering the output of said first filter means and for outputting a signal in a band-pass region determined by said predetermined frequency band of interest; and
   output means for calculating the variance of rhythmic oscillations in the signal outputted by said second filter means.

2. The system according to claim 1 wherein said predetermined frequency band of interest is associated with respiratory activity.

3. The system according to claim 1 further comprising:
   a compensator means for receiving the intervals read out from said buffer means and adjusting said intervals between said event in successive heartbeats to within a predetermined range.

4. A system according to claim 1 wherein said first filter means comprises:
   a moving polynomial filter constructed on the basis of a 2m+1 point polynomial of order n whereby said aperiodic portion of said intervals read out is determined and subtracted from said intervals read out to produce a residual signal to be outputted as said output of said first filter means to said second filter means.

5. The system according to claim 4 wherein m=10 and n=3.

6. The system according to claim 4 wherein m=25 and n=3.

7. The system according to claim 4, wherein n=3 and 2m+1 samples occur over a time period of approximately twice the interval between respiratory cycles.

8. The system according to claim 4, wherein n=3 and 2m+1 samples occur over a time period of approximately twice the interval between oscillations.

9. The system according to claim 1, wherein said predetermined frequency band of interest is associated with oscillations in blood pressure, vasomotor activity, electrodermal activity or electroencephalographic activity.

10. A system for detecting amplitude variations in the rhythmic oscillations of a physiological response pattern occurring in a predetermined frequency band of interest, comprising:
    sensor means for detecting said physiological response pattern and outputting a signal based on said response pattern;
    analog-to-digital converting means for converting said output signal of said sensor means into a digital output, wherein a sampling frequency of said analog-to-digital converting means is determined by said frequency band of interest;
    first filter means responsive to the output of said analog-to-digital converting means, including means for determining an aperiodic portion of said physiological response pattern from said output of said analog-to-digital converting means and a subtraction means for subtracting said aperiodic portion from said output of said analog-to-digital converting means and producing a corresponding output;
    second filter means for receiving and filtering the output of said first filter means and for outputting a signal in a band-pass region determined by said predetermined frequency band of interest; and
    output means for calculating the variance of rhythmic oscillations in the signal outputted by said second filter means.

11. The system according to claim 10 wherein a plurality of physiological response patterns are detected and wherein said output means further includes a coherence measurement means for providing a weighted coherence between the calculated variance of each of said response patterns occurring in said predetermined frequency band of interest.

12. The system according to claim 10 wherein said predetermined frequency band of interest is associated with respiratory activity.

13. The system according to claim 10 further comprising:
    a compensator means for receiving the output of said analog-to-digital converting means and adjusting said analog-to-digital converting means output to within a predetermined range.

14. A system according to claim 10 wherein said first filter means comprises a moving polynomial filter constructed on the basis of a 2m+1 point polynomial of order n whereby said aperiodic portion of said physiological response pattern is determined and subtracted from said physiological response pattern to produce a residual signal to be outputted as said output of said first filter means to said second filter means.

15. The system according to claim 14 wherein m=10 and n=3.

16. The system according to claim 14 wherein m=25 and n=3.

17. The system according to claim 14, wherein n=3 and 2m+1 samples occur over a time period of approximately twice the interval between respiratory cycles.

18. The system according to claim 14 wherein n=3 and 2m+1 samples occur over a time period of approximately twice the interval between oscillations associated with blood pressure, vasomotor activity, electrodermal activity or electroencephalographic activity.

19. The system according to claim 10, wherein said predetermined frequency band of interest is associated with oscillations in blood pressure, intracranial pressure, vasomotor activity, electrodermal activity or electroencephalographic activity.

20. A method for detecting amplitude variations in the rhythmic oscillations of heart period in a predetermined frequency band of interest, comprising the steps of:
  detecting the occurrence of an event in a cycle of a heartbeat;
  determining the time intervals between the occurrence of said event in successive heartbeats;
  storing said determined time intervals;
  reading out said stored intervals at predetermined time intervals;
  performing a first filtering function on said intervals read out including removing an aperiodic portion of said read out intervals;
  receiving and filtering said first filtered read out intervals with said aperiodic portion removed therefrom and outputting a signal in a band-pass region determined by said predetermined frequency band of interest; and
  calculating the variance of rhythmic oscillations in said signal outputted in said receiving and filtering step.

21. The method according to claim 20 wherein the step of storing said determined intervals includes the step of compensating for said determined intervals which are outside of a predetermined range so that all intervals are within said predetermined range.

22. The method according to claim 20 wherein the step of performing a first filtering function includes the step of determining the aperiodic portion of said read out interval through the use of a moving polynomial filter based upon a polynomial equation having $2m+1$ points and being of the nth order.

23. The method according to claim 22 where $m=10$ and $n=3$.

24. The method according to claim 22 where $m=25$ and $n=3$.

25. A method for detecting amplitude variations in the rhythmic oscillations of a physiological response pattern occurring in a predetermined frequency band of interest, comprising the steps of:
  detecting said physiological response pattern;
  converting said response pattern into a digital output by sampling said response pattern at a frequency determined by said predetermined frequency band of interest;
  performing a first filtering function on said digital output indicative of said response pattern, including removing an aperiodic portion of said digital output of said response pattern;
  receiving and filtering said first filtered digital output with said aperiodic portion removed therefrom and outputting a signal in a band-pass region determined by said predetermined frequency band of interest; and
  calculating the variance of rhythmic oscillations in said signal outputted in said receiving and filtering step.

26. The method according to claim 25 wherein:
  the step of converting said response pattern into a digital output includes the step of compensating said digital output to be within a predetermined range.

27. The method according to claim 25 wherein the step of performing a first filtering function includes the step of determining the aperiodic portion of said digital output of said response pattern through the use of a moving polynomial filter based upon a polynomial equation having $2m+1$ points and being of the nth order.

28. The method according to claim 27 where $m=10$ and $n=3$.

29. The method according to claim 27 where $m=25$ and $n=3$.

30. A system for detecting amplitude variations in rhythmic oscillations of a point process in a predetermined frequency band of interest, comprising:
  sensor means for detecting an occurrence of an event in the cycle of each of said rhythmic oscillations;
  timing means for determining time intervals between the occurrence of said events;
  buffer means for storing said intervals determined by said timing means;
  means for reading out said intervals stored in said buffer means at predetermined time intervals;
  first filter means responsive to the stored intervals read out from said buffer means, including a means for determining an aperiodic portion of said intervals read out from said buffer means and a subtraction means for subtracting said aperiodic portion from said intervals read out from said buffer means and for producing a corresponding output;
  second filter means for receiving and filtering the output of said first filter means and for outputting a signal in a band-pass region determined by said predetermined frequency band of interest; and
  output means for calculating the variance of rhythmic oscillations in the signal outputted by said second filter means.

31. A system for detecting amplitude variations in the rhythmic oscillations of a continuous process in a predetermined frequency band of interest, comprising:
  sensor means for detecting said continuous process and outputting a signal based on the detected continuous process;
  analog-to-digital converting means for converting said output signal of said sensor means into a digital output, wherein a sampling frequency of said analog-to-digital converting means is determined by said frequency band of interest;
  first filter means responsive to the output of said analog-to-digital converting means, including an aperiodic portion determining means for determining an aperiodic portion of said output of said analog-to-digital converting means and a subtraction means for subtracting said aperiodic portion from said output of said analog-to-digital converting means and for producing a corresponding output;
  second filter means for receiving and filtering the output of said first filter means and for outputting a signal in a band-pass region determined by said predetermined frequency band of interest; and
  output means for calculating the variance of rhythmic oscillations in the signal outputted by said second filter means.

32. A method for detecting amplitude variations in the rhythmic oscillations of a continuous process in a predetermined frequency band of interest, comprising the steps of:
  detecting said continuous process;
  converting said detected process into a digital output by sampling said process at a frequency determined by said predetermined frequency band of interest;
  performing a first filtering function on said digital output of said converting step, including removing an aperiodic portion of said digital output of said continuous process;

receiving and filtering said first filtered digital output with said aperiodic portion removed therefrom and outputting a signal in a band-pass region determined by said predetermined frequency band of interest; and calculating the variance of rhythmic oscillations in said signal outputted in said receiving and filtering step.

33. A method for detecting amplitude variations in the rhythmic oscillations of a point process in a predetermined frequency band of interest, comprising the steps of:

detecting the occurrence of events in said point process;

determining the time intervals between the occurrence of successive events in said point process;

storing said determined time intervals;

reading out said stored intervals at predetermined time intervals;

performing a first filtering function on said intervals read out including removing an aperiodic portion of said read out intervals to produce a first filtered signal;

receiving and filtering the first filtered signal and outputting a signal in a band-pass region determined by said predetermined frequency band of interest; and calculating the variance of rhythmic oscillations in said signal outputted in said receiving and filtering step.

34. A system for detecting amplitude variations in rhythmic oscillations of a plurality of signals in a predetermined frequency band of interest, wherein each of said rhythmic oscillations occurs in one of a point process and a continuous process which are represented by respective signals, comprising:

first sensor means for detecting an occurrence of a plurality of events in the cycle of each of said rhythmic oscillations occurring in said point process;

second sensor means for detecting and evaluating said continuous process of each of said rhythmic oscillations occurring in said continuous process and for outputting an output signal based thereon;

timing means responsive to the occurrence of each event detected by said first sensor means for determining time intervals between the occurrence of successive of said events;

buffer means for storing said intervals determined by said timing means;

means for reading out said intervals stored in said buffer means at predetermined time intervals;

analog-to-digital converting means for converting said output signal of said second sensor means into a digital output, wherein a sampling frequency of said analog-to-digital converting means is determined by said frequency band of interest;

first filter means responsive to the output of said analog-to-digital converting means and said intervals read out from said buffer means, including means for determining an aperiodic portion of at least one of said intervals read out and the output of said analog-to-digital converting means and subtraction means for subtracting said aperiodic portion of at least one of said intervals read out and said output of said analog-to-digital converting means from at least one of said intervals read out of said buffer means and said output of said analog-to-digital converting means and for producing a corresponding output;

second filter means for receiving and filtering the output of said first filter means and for outputting a signal in a band-pass region determined by said predetermined frequency band of interest;

output means for calculating the variance of rhythmic oscillations in the signal outputted by said second filter means; and a coherence measurement means for providing a weighted coherence between the calculated variance of any two of said rhythmic oscillations.

35. A system according to claim 34, wherein said predetermined frequency band of interest is associated with respiratory activity and the point process signal is a heartbeat period signal and the continuous process signal is a respiration signal.

* * * * *

UNITED STATES PATENT AND TRADEMARK OFFICE
CERTIFICATE OF CORRECTION

PATENT NO. : 4,510,944

DATED : April 16, 1985

INVENTOR(S) : STEPHEN W. PORGES

It is certified that error appears in the above-identified patent and that said Letters Patent is hereby corrected as shown below:

On page 1, [76], delete "1407 Grandview Champaign, Ill. 61820" and insert therefor --4805 Enfield Road, Bethesda, MD 20814--;

On page 1, column 2, line 12, delete "Kitney et al.," line 13, after "Neuropathy" delete ";" and insert therefor --Kitney et al.,--;

On page 1, column 2, line 15, delete "Sayers;" and after "Variability" delete ";" and insert therefor --Sayers--;

On page 1, in the diagram below, block 11, delete "OUTLINER" and insert therefor --OUTLIER--;

On page 1, in the diagram below, block 96, second line, delete "CALCULATIONS" and insert therefor --CALCULATION--;

UNITED STATES PATENT AND TRADEMARK OFFICE
CERTIFICATE OF CORRECTION

PATENT NO. : 4,510,944

DATED : April 16, 1985

INVENTOR(S) : STEPHEN W. PORGES

It is certified that error appears in the above-identified patent and that said Letters Patent is hereby corrected as shown below:

On page 1, line 32 (i.e., line 11 of the ABSTRACT) delete "band pass" and insert therefor --bandpass--;

On sheet 2 of 4, in FIG. 2a, block 11, delete "OUTLINER" and insert therefor --OUTLIER--;

On sheet 2 of 4, in FIG. 2a, block 96, second line, delete "CALCULATIONS" and insert therefor --CALCULATION--;

In column 1, line 8, change "MH-0054" to --MH-00054--;

In column 3, line 34, delete "what" and insert therefor --which--;

In column 3, line 36, delete "that" and insert therefor --the--;

In column 5, line 54, delete "with";

UNITED STATES PATENT AND TRADEMARK OFFICE
CERTIFICATE OF CORRECTION

PATENT NO. : 4,510,944

DATED : April 16, 1985

INVENTOR(S) : STEPHEN W. PORGES

It is certified that error appears in the above—identified patent and that said Letters Patent is hereby corrected as shown below:

In column 5, line 59, delete "from resulting" and insert therefore --resulting from-- and after "subtracting" delete "of";

In column 5, line 61, delete "FIG. 2 is a" and insert therefore --FIGS. 2a and 2b are-- and after "block" delete "diagram" and insert therefore --diagrams--;

In column 7, line 18, delete "to" and insert therefore --which--;

In column 7, line 51, delete "problem" and insert therefore --problems--;

In column 8, line 50, delete "in";

In column 10, line 21, delete "ao" and insert therefore --$a_0$--;

In column 10, line 41, delete "ao" and insert therefore --$a_0$--;

UNITED STATES PATENT AND TRADEMARK OFFICE
CERTIFICATE OF CORRECTION

PATENT NO. : 4,510,944

DATED : April 16, 1985

INVENTOR(S) : STEPHEN W. PORGES

It is certified that error appears in the above-identified patent and that said Letters Patent is hereby corrected as shown below:

In column 10, line 43, delete "$a_O$" and insert therefore --$a_0$--;

In column 10, line 48, delete "$a_O$" and insert therefore --$a_0$--;

In column 11, delete lines 8-47 and insert therefore

```
--     PROGRAM TRY(INPUT,OUTPUT)
       DIMENSION A(100)
       READ *,N1,N2
       CALL POLMOV(N1,N2,A)
       PRINT 50,(A(I),I=1,N2)
    50 FORMAT(10F8.5)
       STOP
       END
       SUBROUTINE POLMOV(N1,N2,A)
C COMPUTES MOVING POLYNOMIAL FILTER COEFFICIENTS FOR
C POLYNOMIALS OF DEGREE N1 (2 .LE. N1  .LE. 5) BASED
C ON A TOTAL OF N2 POINTS.
       DIMENSION A(N2)
       IF(N1.LT.2 .OR. N1.GT.5) RETURN
       IF(N1+1 .GT. N2) RETURN
       IF(2*(N2/2) .EQ. N2) N2= N2-1
       N3= N2/2
       A0= N2
       A2= 0.
       A4= 0.
       A6= 0.
       A8= 0.
       DO 1 I= 1,N3
       AI=I
```

UNITED STATES PATENT AND TRADEMARK OFFICE
CERTIFICATE OF CORRECTION

PATENT NO. : 4,510,944

DATED : April 16, 1985

INVENTOR(S) : STEPHEN W. PORGES

It is certified that error appears in the above-identified patent and that said Letters Patent is hereby corrected as shown below:

```
       A2= A2+ 2.* AI**2
       A4= A4+ 2.* AI**4
       A6= A6+ 2.* AI**6
    1  A8= A8+ 2.* AI**8
       IF(N1 .GT. 3) GOTO 45
       AJ= -N3-1
       DEN= A0*A4-A2*A2
       DEN= 1./DEN
       DO 2 I= 1,N2
       AJ= AJ+1.
       AJ2= AJ*AJ
    2  A(I)= DEN*(A4-AJ2*A2)
       RETURN
       DEN= A0*A4*A8+2.*A2*A4*A6-A4**3-A0*A6*A6-A2*A2*A8
   45  DEN= 1./DEN
       C1= A4*A8-A6*A6
       C2= A4*A6-A2*A8
       C3= A2*A6-A4*A4
       AJ= -N3-1
       DO 3 I= 1,N2
       AJ= AJ+1.
    3  A(I)= DEN*(C1+C2*AJ*AJ+C3*AJ**4)
       RETURN
       END
```

In column 12, line 42, delete "data points";

In column 13, line 14, delete "in";

UNITED STATES PATENT AND TRADEMARK OFFICE
CERTIFICATE OF CORRECTION

PATENT NO. : 4,510,944

DATED : April 16, 1985

INVENTOR(S) : STEPHEN W. PORGES

It is certified that error appears in the above—identified patent and that said Letters Patent is hereby corrected as shown below:

In column 14, line 17, delete "ete" and insert therefore --et--;

In column 16, line 50, delete "1O" and insert therefore --10--.

Signed and Sealed this

Eighth Day of July 1986

[SEAL]

Attest:

Attesting Officer

DONALD J. QUIGG

Commissioner of Patents and Trademarks